(12) United States Patent
Zhang et al.

(10) Patent No.: US 11,978,190 B2
(45) Date of Patent: May 7, 2024

(54) RAPID DETECTION SYSTEM FOR WATER AND IMPURITY OF MACHINE-HARVESTED SEED COTTON IN PURCHASE LINK

(71) Applicant: Shihezi University, Xinjiang (CN)

(72) Inventors: Ruoyu Zhang, Xinjiang (CN); Long Wan, Xinjiang (CN); Yinglan Jiang, Xinjiang (CN); Mengyun Zhang, Xinjiang (CN); Jinqiang Chang, Xinjiang (CN); Fangdan Song, Xinjiang (CN)

(73) Assignee: Shihezi University, Xinjiang (CN)

( * ) Notice: Subject to any disclaimer, the term of this patent is extended or adjusted under 35 U.S.C. 154(b) by 378 days.

(21) Appl. No.: 17/409,967

(22) Filed: Aug. 24, 2021

(65) Prior Publication Data
US 2022/0067912 A1    Mar. 3, 2022

(30) Foreign Application Priority Data
Aug. 27, 2020   (CN) .......................... 202010877583.1

(51) Int. Cl.
*G06T 7/00*   (2017.01)
*B65G 17/12*  (2006.01)
(Continued)

(52) U.S. Cl.
CPC ............ *G06T 7/0004* (2013.01); *B65G 17/12* (2013.01); *G01N 5/00* (2013.01); *G01N 21/95* (2013.01);
(Continued)

(58) Field of Classification Search
CPC ........ B65G 17/12; B65G 49/00; B65G 63/00; G01N 2021/8592; G01N 21/84;
(Continued)

(56) References Cited

U.S. PATENT DOCUMENTS 5,917,927 A * 6/1999 Satake .................... G01N 21/85
382/110
6,567,538 B1 * 5/2003 Pelletier ............. G01N 21/8915
382/224
(Continued)

FOREIGN PATENT DOCUMENTS

| CN | 106405065 A * | 2/2017 | ............. G01N 33/48 |
| CN | 107621468 A * | 1/2018 | ............. G01N 21/88 |

(Continued)

*Primary Examiner* — David L Singer
(74) *Attorney, Agent, or Firm* — Faegre Drinker Biddle & Reath LLP

(57) ABSTRACT

A rapid detection system for water and impurity of machine-harvested seed cotton in purchase link, including: a seed cotton large-impurity-cleaning device, a seed cotton sample case, a driving and transmission device, a cotton pressing device, an image collection and processing device, and a moisture regain rate detection device and a control cabinet. The seed cotton sample case consists of a positioning plate and a high light transmittance glass case, the weighing device consists of a weighing sensor, a pallet, and an electric push rod. The driving and transmission device consists of the rollers, the motor of conveyor belts and conveyor belts, the cotton pressing device consists of an electric push rod, a connecting rod, a connecting plate, and a high light transmittance glass plate. Said rapid detection system could realize the rapid detection to the impurity rate and moisture regain rate of the seed cotton.

6 Claims, 5 Drawing Sheets

(51) Int. Cl.
  *G01N 5/00* (2006.01)
  *G01N 21/95* (2006.01)
  *G01N 33/00* (2006.01)
  *H04N 23/90* (2023.01)

(52) U.S. Cl.
  CPC ......... *G01N 33/0098* (2013.01); *H04N 23/90* (2023.01); *G06T 2207/20081* (2013.01)

(58) Field of Classification Search
  CPC .... G01N 21/85; G01N 21/95; G01N 33/0098; G01N 5/00; G06T 2207/20081; G06T 2207/30124; G06T 7/0004; H04N 23/80; H04N 23/90
  See application file for complete search history.

(56) References Cited

U.S. PATENT DOCUMENTS

2017/0122925 A1* 5/2017 Righettini ............ G01N 33/365
2020/0015409 A1* 1/2020 de Bruin ............... G06T 7/0004

FOREIGN PATENT DOCUMENTS

CN       110646354 A  *  1/2020  ............. G01N 21/27
JP       2001041895 A *  2/2001  ............. G01N 21/85

* cited by examiner

RAPID DETECTION SYSTEM FOR WATER AND IMPURITY OF MACHINE-HARVESTED SEED COTTON IN PURCHASE LINK

CROSS REFERENCE OF RELATED APPLICATION

The present application claims priority to Chinese Patent Application No. 202010877583.1, titled "RAPID DETECTION SYSTEM FOR WATER AND IMPURITY OF MACHINE-HARVESTED SEED COTTON IN PURCHASE LINK", filed on Aug. 27, 2020 with the China National Intellectual Property Administration, which is incorporated herein by reference in its entirety.

TECHNICAL FIELD

The present application relates to the technical field of agricultural mechanical equipment, in particular to a rapid detection system for water and impurity of machine-harvested seed cotton in purchase link.

BACKGROUND

Cotton is a kind of crucial production material, which has an important impact on the national economy and social development. In the production and sales of cotton, a sales price of cotton will decrease as the content of impurities increases, and the moisture regain rate is an important factor affecting the processing quality of seed cotton.

In the current cotton purchase process in China, an impurity separation test to seed cotton samples is performed for detecting an impurity rate with a cotton impurity analyzer after sampling mainly by manual. A handheld moisture regain rate measuring instrument with manner of manual measurement is generally used in a seed cotton moisture regain rate test, each link of the test requires manual work, which causes high labor intensity, low efficiency, and complicated procedures, and has disadvantages in a rapid detection and classification to seed cotton, so that the production and sales efficiency of seed cotton during purchase is seriously affected. In summary, the present application proposes a set of rapid detection system for water and impurities of machine-harvested seed cotton in purchase link, which realizes rapid detection of the impurity content and moisture regain rate of seed cotton during purchase, improves the degree of automation, reduces manufacturing cost of detection device and labor intensity, and improves detection efficiency.

SUMMARY

In order to overcome deficiencies of the existing technology in purchase link of seed cotton, the present application provides a rapid detection system for water and impurity of machine-harvested seed cotton in purchase link. The technical solutions are as follows.

A rapid detection system for water and impurity of machine-harvested seed cotton in purchase link, wherein said rapid detection system comprises: a seed cotton large-impurity-cleaning device, a seed cotton sample case, a driving and transmission device, a cotton pressing device, an image collection and processing device, a moisture regain rate detection device and a control cabinet; wherein the seed cotton large-impurity-cleaning device is located on a left-most side of the rapid detection system, a cotton inlet is provided at the top of the seed cotton large-impurity-cleaning device and a cotton outlet is provided at the upper part of the right side of the seed cotton large-impurity-cleaning device; the seed cotton sample case is provided right below the cotton outlet of the seed cotton large-impurity-cleaning device, and the seed cotton sample case consists of a positioning plate and a high light transmittance glass case located right above the positioning plate, a weighing device is provided below the positioning plate; the weighing device consists of a weighing sensor, a pallet, and a first electric push rod; the weighing sensor is located on top of the weighing device, and the pallet is provided below the weighing sensor, and the first electric push rod is provided at the lower side of the pallet; the weighing device is provided right below the seed cotton sample case and centrally located between two conveyor belts; the positioning plate is located above the left side of the driving and transmission device, the image collection and processing device and the cotton pressing device are provided at right side of the driving and transmission device;

the driving and transmission device includes the driving roller, the driven roller, the first conveyor belt, the second conveyor belt, and a motor of conveyor belts; the motor of conveyor belts is located below the left side of the driving and transmission device, and an end of a transmission shaft of the motor of conveyor belts is coupled to one end of a driving roller through a belt; a first conveyor belt and a second conveyor belt are paralleled coupled to the driving roller and a driven roller, respectively;

the cotton pressing device consists of a second electric push rod, a connecting rod, a connecting plate, and a high light transmittance glass plate, the image collection and processing device consists of a first camera, a first light source, a first detection sensor, a second camera, a second light source, a second detection sensor, an control cabinet, and a touch screen; the moisture regain rate detection device consists of a moisture regain rate detection sensor, a signal wire, and a measurement controller, the driving and transmission device consists of a driving roller, the driven roller, the first conveyor belt, the second conveyor belt, the motor of conveyor belts, a speed regulator and a detection sensor, the two conveyor belts are in parallel, and a certain gap is provided between two conveyor belts, said two conveyor belts have same driving roller and driven roller, so the speed of these two conveyor belts are same, a detection sensor is mounted on the driving and transmission device.

The cotton pressing device consists of a second electric push rod, a connecting rod, a connecting plate, and a high light transmittance glass plate, the connecting plate is fixed to the electric push rod, and the cotton pressing glass plate is fixed to the connecting plate by the connecting rod, and thus moved downward by the actuation of the electric push rod so as to perform cotton pressing;

the image collection and processing device consists of a first camera, a second camera, a camera bracket, a first light source, a second light source, a detection sensor, an control cabinet and a touch screen; the first camera, the first light source, the second camera and the second light source are all fixed on a rack through the camera bracket, bolts and nuts, so that the positions of the first camera and the first light source, and the positions of the second camera and the second light source are fixed above and below the driving and transmission device, respectively, through the rack so as to collect image information of a seed cotton sample from double sides.

The detection sensor is fixed on the rack. During operation, the image collection device is covered by a hood, and light sources are lighting. After surfaces of the seed cotton being pressed flattened by the cotton pressing device, the cameras collect the image information of the upper and lower surfaces of the seed cotton in real time. After being processed by the image processing software, the impurity content rate is calculated, and the moisture regain rate of the seed cotton sample is detected by a moisture regain rate measurement circuit, and the impurity content and the moisture regain rate are displayed on the touch screen in real time, and the information is stored.

The moisture regain rate detection device consists of a moisture regain rate detection sensor, a signal wire, and a measurement controller. The moisture regain rate detection sensor is fixed in the high light transmittance glass plate, and is communicated with the measurement controller through the signal wire; the measurement controller is provided inside the control cabinet. When the first detection sensor detects a signal, the motor starts running and drives the sample case to the collection site, and then the second detection sensor conducts the sensing, and thus the controller controls the motor to stop running, and a moisture regain rate of the seed cotton is detected by the moisture regain rate detection sensor after a cotton sample being compacted by the cotton pressing device.

For the process of the detection system, the impurity information of the seed cotton in the sample image is processed and analyzed mainly by the image processing and machine learning technology so as to predict the mass of the small impurity. For detecting the total impurity rate of the sample, the total impurity rate of the sample needs to be calculated by combining the mass of the small impurity obtained according to the prediction with the mass of the large impurity obtained by the large-impurity-cleaning device.

The beneficial technical effort of the present application: the disadvantages in the prior art such as the complicated and slow detection process to water and impurity in purchase link of seed cotton can be overcome, and the impurity rate and moisture regain rate of a seed cotton sample can be rapid detected, which favorable supports the rapid classification to seed cotton, overcomes the disadvantages of manual operation and improves work efficiency. The motor with small-power is used for transmission of the equipment, which reduces energy consumption, and has great use value and promotion value.

BRIEF DESCRIPTION OF THE DRAWINGS

Hereinafter, the present application will be further described in detail through specific embodiments in conjunction with the accompanying drawings.

Figure 1:
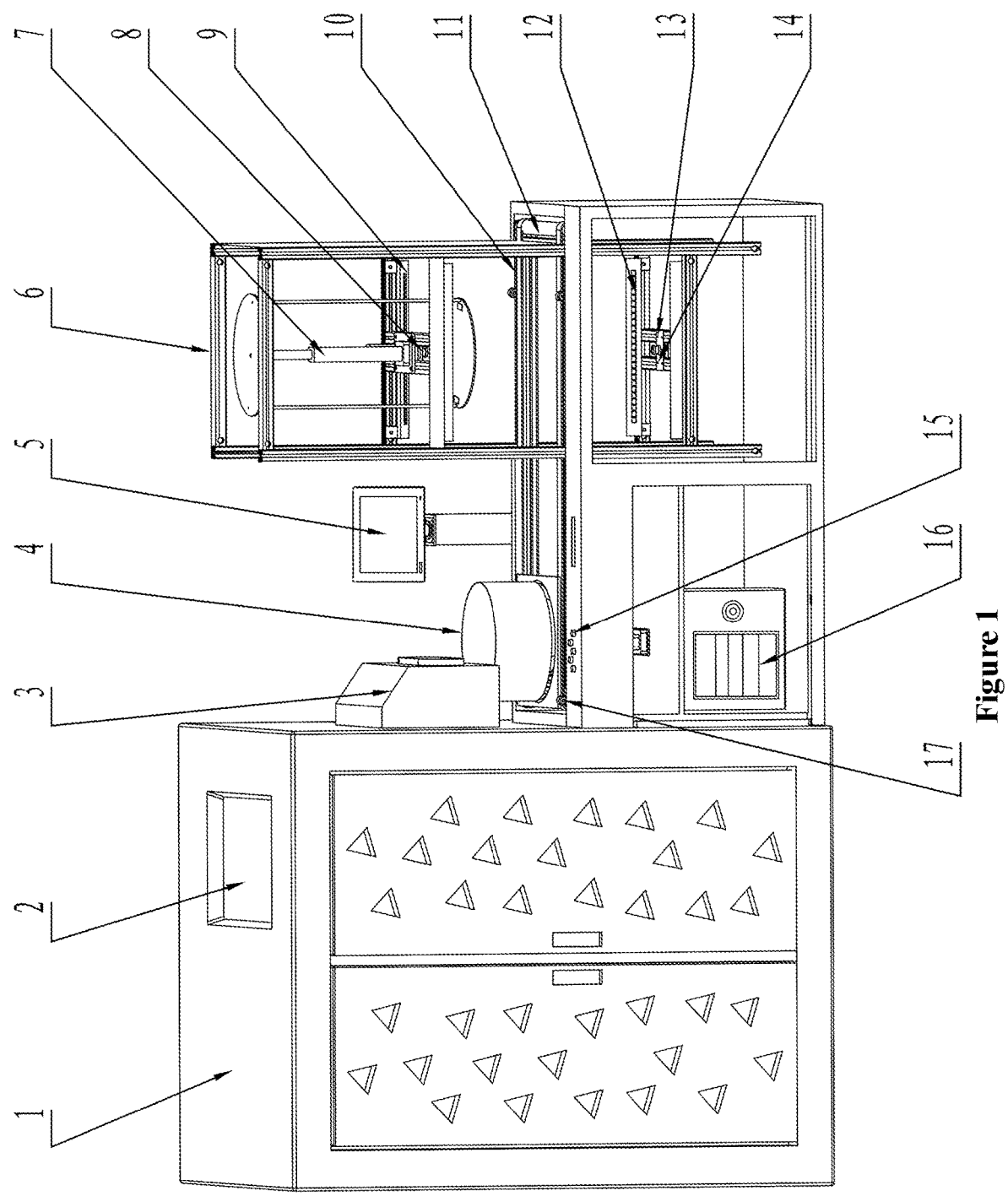
FIG. 1 is a front view of the system of the present application.

Reference numerals in the figures: 1—seed cotton large-impurity-cleaning device, 2—cotton inlet, 3—cotton outlet, 4—seed cotton sample case, 5—touch screen, 6—rack, 7—cotton pressing device, 8—first camera, 9—first light source, 10—second detection sensor, 11—driving and transmission device, 12—second light source, 13—camera bracket, 14—second camera, 15—button switch, 16—control cabinet, 17—first detection sensor, 18—high light transmittance glass case, 19—positioning plate, 20—weighing sensor, 21—first electric push rod, 22—pallet, 23—driving roller, 24—first conveyor belt, 25—second conveyor belt, 26—driven roller, 27—speed regulator, 28—motor of conveyor belts, 29—connecting plate, 30—second electric push rod, 31—connecting rod, 32—moisture regain rate detection sensor, 33—high light transmittance glass plate.

DETAILED DESCRIPTION OF THE EMBODIMENTS

Hereinafter, the present application will be further described in detail through specific embodiments in conjunction with the accompanying drawings.

Figure 2:
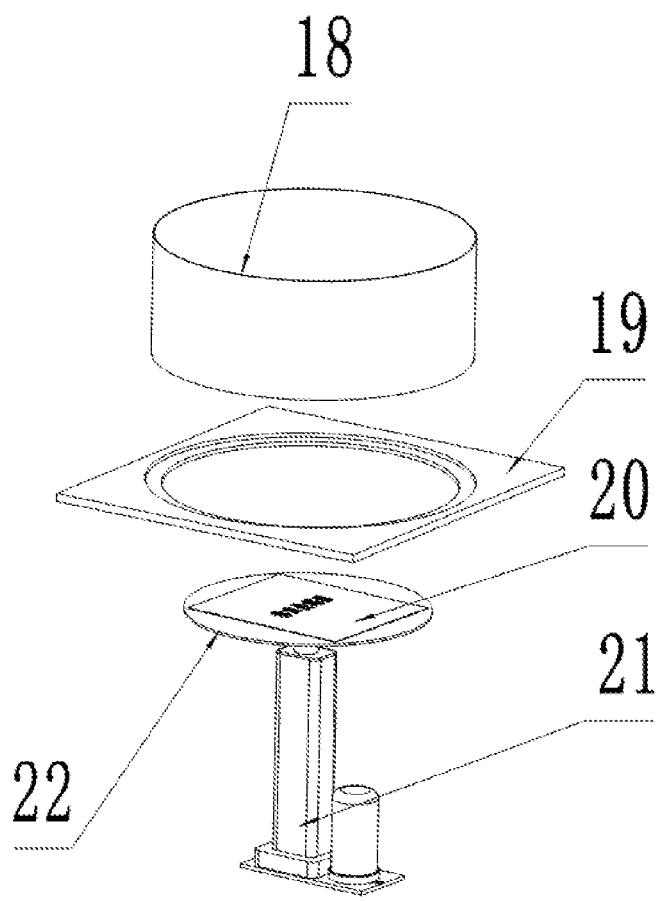
FIG. 2 is a structural view of a weighing device of the present application.
Figure 3:
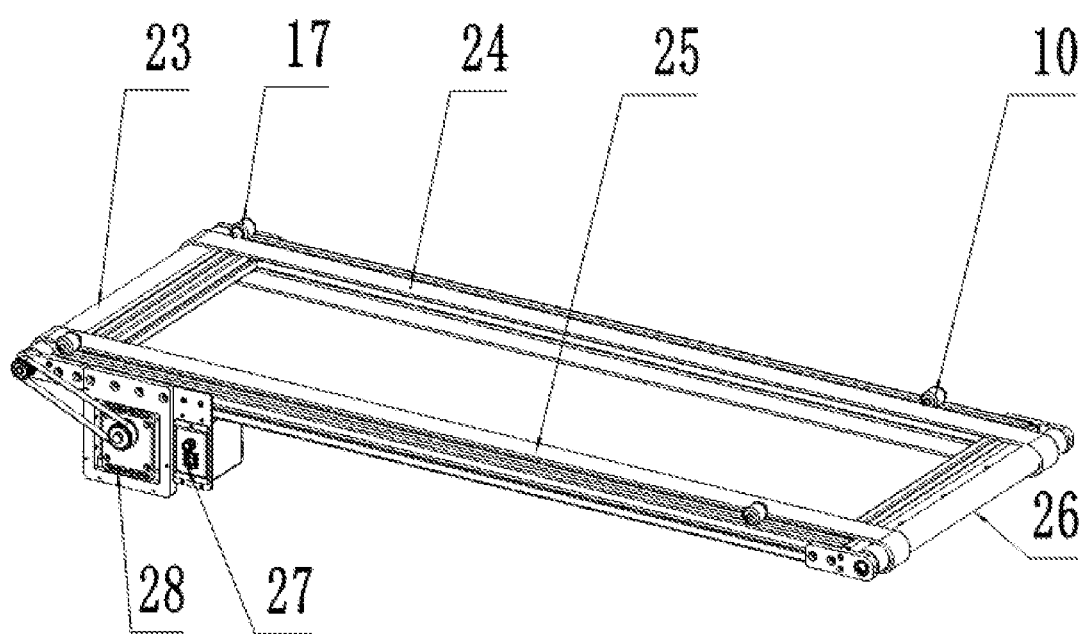
FIG. 3 is a structural view of a driving and transmission device of the present application.
Figure 4:
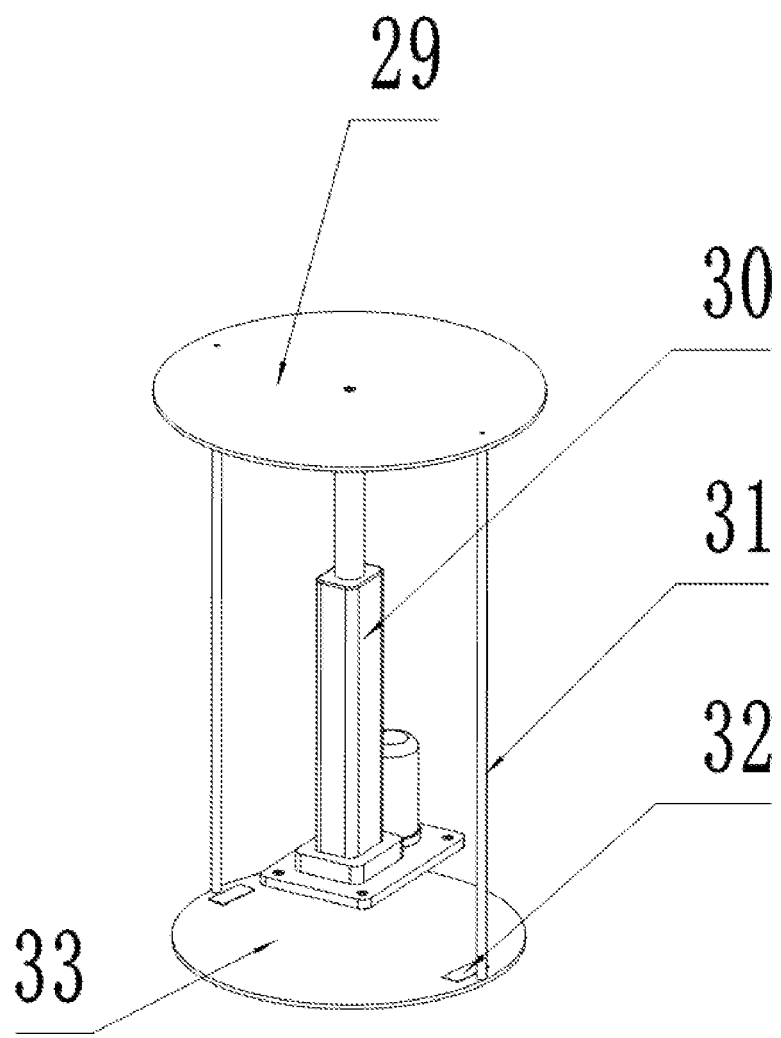
FIG. 4 is a structural view of a cotton pressing device of the present application.
Figure 5:
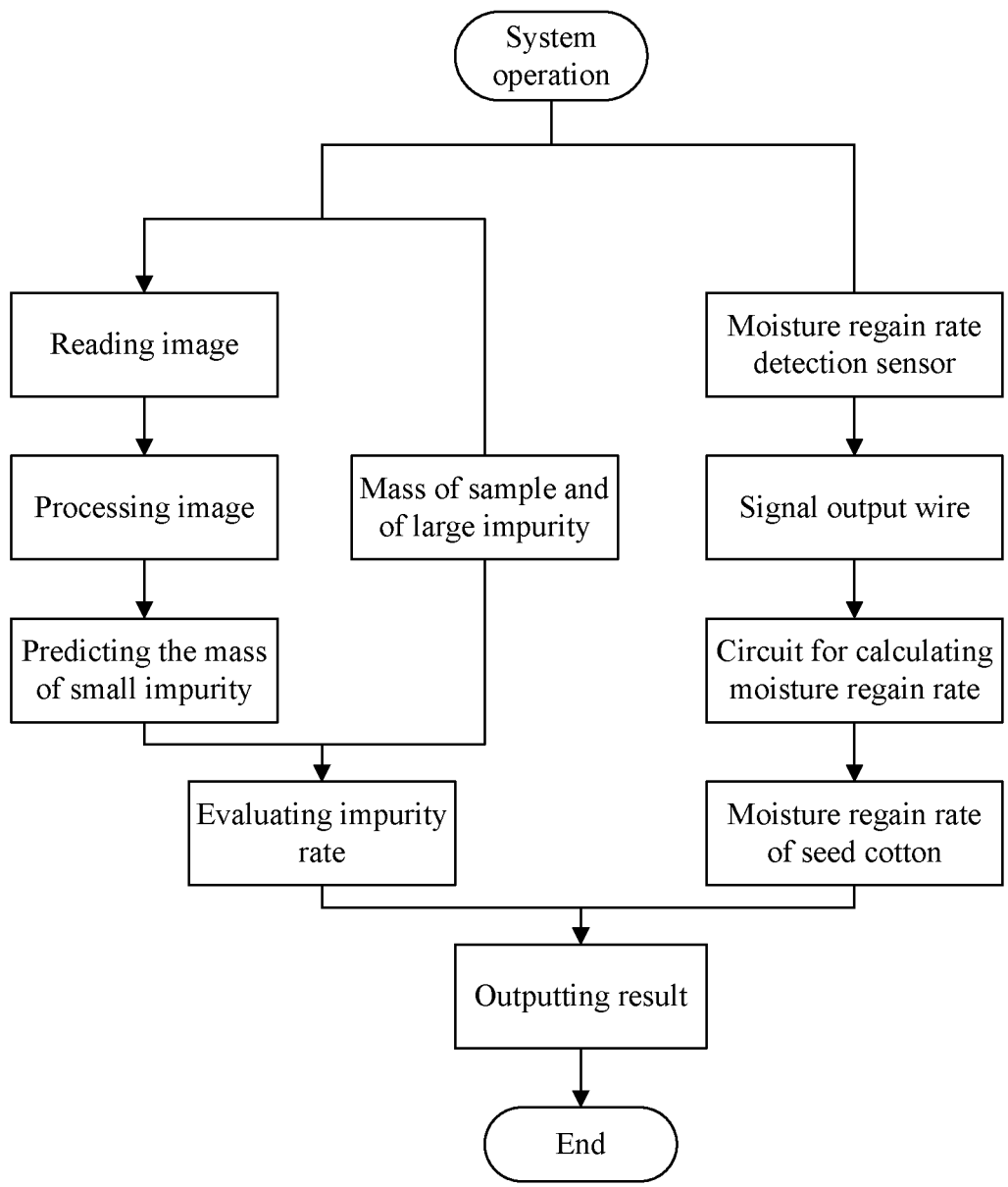
FIG. 5 is a detection flow chart of system of the present application.

As shown in FIG. 1, FIG. 2, FIG. 3, and FIG. 4, a rapid detection system for water and impurity of machine-harvested seed cotton in purchase link consists of a seed cotton large-impurity-cleaning device 1, a seed cotton sample case 4, a driving and transmission device 11, a cotton pressing device 7, an image collection and processing device, a moisture regain rate detection device and a control cabinet 16; the seed cotton large-impurity-cleaning device 1 is located on a leftmost side of the rapid detection system, a cotton inlet 2 is provided at the top of the seed cotton large-impurity-cleaning device 1 and a cotton outlet 3 is provided at the upper right part of the seed cotton large-impurity-cleaning device 1, the seed cotton sample case 4, which is provided right below the cotton outlet 3 of the seed cotton large-impurity-cleaning device, consists of a positioning plate 19 and a high light transmittance glass case 18; the high light transmittance glass case 18 is located right above the positioning plate 19, a weighing device, which is provided below the positioning plate 19, consists of a weighing sensor 20, a pallet 22, and a first electric push rod 21; the weighing sensor 20 is located at the top of the weighing device, and the pallet 22 is provided below the weighing sensor 20, and the first electric push rod 21 is provided at lower side of the pallet 22; the weighing device is provided right below the seed cotton sample case 4 and centrally located between two conveyor belts; the positioning plate 19 is located above the left side of the driving and transmission device 11, and the image collection and processing device and the cotton pressing device are provided at the right side of the driving and transmission device 11;

the driving and transmission device 11 consists of a driving roller 23, a driven roller 26, a first conveyor belt 24, a second conveyor belt 25, and a motor of conveyor belts 28;

A motor of conveyor belts 28 is located lower the left side of the driving and transmission device 11, and an end of the transmission shaft of the motor of conveyor belts is coupled to one end of the driving roller 23 through a belt; the first conveyor belt 24 and the second conveyor belt 25 are paralleled coupled to the driving roller 23 and the driven roller 26, respectively;

the cotton pressing device consists of a second electric push rod 30, a connecting rod 31, a connecting plate 29, and a high light transmittance glass plate 33; the image collection and processing device consists of a first camera 8, a first light source 9, a first detection sensor 17, a second camera 14, a second light source 12, a second detection sensor 10, an control cabinet 16 and a touch screen; the moisture regain rate detection device consists of a moisture regain rate detection sensor 32, a signal wire, and a measurement controller; the seed cotton sample case consists of a positioning plate and a high light transmittance glass case. A stepped round hole with a diameter slightly smaller than that of the high light transmittance glass case is opened on the center of the positioning plate so as to realize the collection of information images on the lower surface of the seed cotton sample. The positioning plate is fixed on the conveyer belt, which has an initial position below the cotton outlet. The high light transmittance glass case is placed on the positioning plate. The weighing device 20 tops up the high light transmittance glass case and weighs the seed cotton when falling down; the weighing device consists of a weighing sensor, a pallet and an electric push rod. The weighing sensor is mounted on the pallet, which is fixed on the first electric push rod. The diameter of the pallet is slightly smaller than that of said round hole of the positioning plate, which facilitates to top up the high light transmittance glass case by the pallet with the electric push rod so as to conduct the detection when the seed cotton with large impurity being removed falls on the weighing sensor.

The driving and transmission device consists of the driving roller, the driven roller, the first conveyor belt, the second conveyor belt, the motor of conveyor belts, a speed regulator and a detection sensor, where the two conveyor belts are in parallel, and a certain gap is provided between two conveyor belts. Said two conveyor belts have same driving roller and driven roller, so the speed of these two conveyor belts are same. A detection sensor is mounted on the driving and transmission device.

The cotton pressing device consists of a second electric push rod, a connecting rod, a connecting plate, and a high light transmittance glass plate. The connecting plate is fixed to the electric push rod, and the cotton pressing glass plate is fixed to the connecting plate by the connecting rod, and thus moved downward by the actuation of the electric push rod so as to perform cotton pressing.

The image collection and processing device consists of a first camera, a second camera, and a camera bracket, a first light source, a second light source, a detection sensor, an control cabinet and a touch screen; the first camera, the first light source, the second camera and the second light source are all fixed on a rack through the camera bracket, bolts and nuts, so that the positions of the first camera and the first light source, and the positions of the second camera and the second light source are fixed above and below the driving and transmission device, respectively, through the rack so as to collect image information of a seed cotton sample from double sides. The detection sensor is fixed on the rack. During operation, the image collection device is covered by a hood, and light sources are lighting. After surfaces of the seed cotton being pressed flattened by the cotton pressing device, the cameras collect the image information of the upper and lower surfaces of the seed cotton in real time. After being processed by the image processing software, the impurity content rate is calculated, and the moisture regain rate of the seed cotton sample is detected by a moisture regain rate measurement circuit, and the impurity content and the moisture regain rate are displayed on the touch screen in real time, and the information is stored.

The moisture regain rate detection device consists of a moisture regain rate detection sensor, a signal wire, and a measurement controller. The moisture regain rate detection sensor is fixed in the high light transmittance glass plate, and is communicated with the measurement controller through the signal wire; the measurement controller is provided inside the control cabinet. When the first detection sensor detects a signal, the motor starts running and drives the sample case to the collection site, and then the second detection sensor conducts the sensing, and thus the controller controls the motor to stop running, and a moisture regain rate of the seed cotton is detected by the moisture regain rate detection sensor after the cotton sample being compacted by the cotton pressing device.

For the process of the detection system, the impurity information of the seed cotton in the sample image is processed and analyzed mainly by the image processing and machine learning technology so as to predict the mass of the small impurity. For detecting the total impurity rate of the sample, the total impurity rate of the sample needs to be calculated by combining the mass of the small impurity obtained according to the prediction with the mass of the large impurity obtained by the large-impurity-cleaning device.

Sample seed cotton is fed from the cotton inlet of the seed cotton large-impurity-cleaning device, and the seed cotton with the large impurity being removed falls into the seed cotton sample case through the cotton outlet. The mass of the seed cotton with the large impurity being removed is recorded by the weighing sensor, and after that the switch button is pressed. Then the first electric push rod descends, and the sample glass case falls on the positioning plate. When the first detection sensor detects a signal, the motor of conveyor belts starts running, that is, the conveyor belt is actuated, and the driving and transmission device transmits the sample case with seed cotton to the image collection site, and then the second detection sensor may conduct the detection. When the second detection sensor detects a signal, that is, the sample case has arrived at a designated site, the controller controls the motor to stop running. After a short delay, the cotton pressing device is moved downward driven by the second electric push rod so as to compact the seed cotton with the large impurity being removed and ensure that the surface of the seed cotton is within one plane. The first camera and the second camera collect real-time image information of a seed cotton sample from double sides in the sample case. The whole image collection device is covered by a hood. After processing by the image processing software, the impurity content rate is calculated, and the moisture regain rate of the seed cotton sample is detected by a moisture regain detection sensor and information is stored, and the impurity content and the moisture regain rate are displayed on the touch screen. After the completion of the, the electric push rod is returned, that is, the cotton pressing device is reset. After a certain delay, the motor of conveyor belts starts to running in reverse direction. When the first detection sensor detects a signal, the motor of conveyor belts stops running, and the weighing device resets and top up the high light transmittance glass case to be standby for the next sample test.

The above uses specific examples above are used to illustrate the present application, which are only used to help to understand the present application, not intending to limit the present application. All equivalent or simple changes variation made in accordance with the structure, feature and principle described taught by in the concept principle of the present application are included in the protection scope of the present application.

The invention claimed is:

1. A rapid detection system for water and impurity of machine-harvested seed cotton in purchase link, said rapid detection system comprising:
   a seed cotton large-impurity-cleaning device;
   a seed cotton sample case;
   a driving and transmission device comprising a driving roller, a driven roller, two conveyor belts, and a motor;
   a cotton pressing device;
   an image collection and processing device;
   a moisture regain rate detection device;
   a weighing device comprising a weighing sensor, a pallet, and a first electric push rod; and
   a control cabinet;
   wherein:
      the seed cotton large-impurity-cleaning device is located on a leftmost side of the rapid detection system, a cotton inlet is provided at the top of the seed cotton large-impurity-cleaning device and a cotton outlet is provided at the upper part of the right side of the seed cotton large-impurity-cleaning device;
      the seed cotton sample case is provided right below the cotton outlet of the seed cotton large-impurity-cleaning device, and the seed cotton sample case includes a positioning plate and a high light transmittance glass case located right above the positioning plate, the weighing device is provided below the positioning plate, and a stepped round hole with a diameter slightly smaller than that of the high light transmittance glass case is opened on a center of the positioning plate, and the high light transmittance glass case is able to be arranged on the stepped round hole;
   the weighing sensor is located on top of the weighing device, the pallet is provided below
   the weighing sensor, and the first electric push rod is provided at the lower side of the pallet;
      the weighing device is provided right below the seed cotton sample case and centrally located between the two conveyor belts;
      the positioning plate is located above the left side of the driving and transmission device, and the positioning plate is fixed on the two conveyor belts, and the image collection and processing device and the cotton pressing device are provided at the right side of the driving and transmission device;
      the motor of the two conveyor belts is located low on the left side of the driving and transmission device, and an end of a transmission shaft of the motor for the two conveyor belts is coupled to one end of the driving roller through a belt; and
      a first conveyor belt and a second conveyor belt of the two conveyor belts are coupled to the driving roller and the driven roller, respectively.

2. The rapid detection system for water and impurity of machine-harvested seed cotton in purchase link according to claim 1, wherein the driving and transmission device further includes a speed regulator and a first detection sensor.

3. The rapid detection system for water and impurity of machine-harvested seed cotton in purchase link according to claim 2, wherein the cotton pressing device further includes a second electric push rod, a connecting rod, a connecting plate, and a high light transmittance glass plate.

4. The rapid detection system for water and impurity of machine-harvested seed cotton in purchase link according to claim 3, wherein the image collection and processing device includes a first camera, a second camera, a camera bracket, a first light source, a second light source, a second detection sensor, and a touch screen; wherein the first camera, the first light source, the second camera and the second light source are all fixed on a rack through the camera bracket, bolts and nuts, so that the positions of the first camera and the first light source and the positions of the second camera and the second light source are fixed above and below the driving and transmission device by the rack, respectively.

5. The rapid detection system for water and impurity of machine-harvested seed cotton in purchase link according to claim 4, wherein the moisture regain rate detection device includes a moisture regain rate detection sensor, a signal wire, and a measurement controller, wherein the moisture regain rate detection sensor is fixed in the high light transmittance glass plate, and is configured to communicate with the measurement controller through the signal wire;
   wherein the measurement controller is fixed inside the control cabinet;
   wherein the measurement controller is configured to start the motor running so as to transit the seed cotton sample case to a collection site when the first detection sensor detects a signal, and to stop the motor running when the second detection sensor detects a signal; and
   wherein a moisture regain rate of the seed cotton is detected by the moisture regain rate detection sensor after the cotton sample being pressed flattened by the cotton pressing device.

6. The rapid detection system for water and impurity of machine-harvested seed cotton in purchase link according to claim 5,
   wherein the image collection and processing device is configured to process utilizing machine learning technology a sample image of the seed cotton so as to predict the mass of a small impurity and detect the total impurity rate of the seed cotton sample,
   wherein the total impurity rate of the seed cotton sample is calculated by combining the mass of the small impurity obtained according to the prediction with the mass of the large impurity obtained by the large-impurity-cleaning device.

* * * * *